(12) United States Patent
Lura et al.

(10) Patent No.: US 10,561,779 B2
(45) Date of Patent: Feb. 18, 2020

(54) INFUSATE CONTAINERS

(71) Applicant: Medtronic, Inc., Minneapolis, MN (US)

(72) Inventors: David B. Lura, Maple Grove, MN (US); Thomas E. Meyer, Stillwater, MN (US); Jin Huang, Shanghai (CN); Yue Qiang Xue, Shanghai (CN)

(73) Assignee: Medtronic, Inc., Minneapolis, MN (US)

( * ) Notice: Subject to any disclaimer, the term of this patent is extended or adjusted under 35 U.S.C. 154(b) by 94 days.

(21) Appl. No.: 15/593,437

(22) Filed: May 12, 2017

(65) Prior Publication Data
US 2018/0326140 A1 Nov. 15, 2018

(51) Int. Cl.
*A61M 1/16* (2006.01)
*A61K 33/14* (2006.01)
*A61K 33/00* (2006.01)

(52) U.S. Cl.
CPC ........... *A61M 1/1668* (2014.02); *A61K 33/00* (2013.01); *A61K 33/14* (2013.01); *A61M 1/1666* (2014.02); *A61M 2205/584* (2013.01); *A61M 2205/6081* (2013.01); *A61M 2205/7545* (2013.01); *A61M 2209/084* (2013.01)

(58) Field of Classification Search
CPC .................................................. A61M 1/1666
See application file for complete search history.

(56) References Cited

U.S. PATENT DOCUMENTS

| | | | |
|---|---|---|---|
| 4,747,822 A | 5/1988 | Peabody | |
| 4,950,230 A | 8/1990 | Kendell | |
| 5,032,265 A | 7/1991 | Jha | |
| 5,141,493 A | 8/1992 | Jacobsen | |
| 5,643,201 A | 7/1997 | Peabody | |
| 5,794,669 A * | 8/1998 | Polaschegg | A61M 1/1656 141/100 |
| 5,972,223 A * | 10/1999 | Jonsson | A61L 2/0023 137/88 |
| 2010/0069817 A1 | 3/2010 | Falkvall | |
| 2010/0078092 A1 | 4/2010 | Weilhoefer | |

(Continued)

FOREIGN PATENT DOCUMENTS

| | | |
|---|---|---|
| CN | 202105667 | 1/2012 |
| DE | 202014104252 | 12/2015 |

(Continued)

OTHER PUBLICATIONS

[NPL637] International Search Report, Application PCT/US2016/043935, dated Feb. 2, 2017.

(Continued)

*Primary Examiner* — Patrick Orme
(74) *Attorney, Agent, or Firm* — Kenneth Collier; Roger Hahn

(57) ABSTRACT

The invention relates to infusate containers and related systems and methods for housing infusates that can be added to a fluid flow path for use during dialysis. The infusate containers can include a filter partitioning the containers into a first and second compartment, a draw tube for drawing up fluid from a bottom portion, a cap, a fluid connector for delivery and withdrawal of fluid from the two compartments, and a fluid connector for connection to a dialysis system.

23 Claims, 9 Drawing Sheets

(56) References Cited

U.S. PATENT DOCUMENTS

| | | |
|---|---|---|
| 2010/0312172 A1 | 12/2010 | Hoffman |
| 2012/0199205 A1* | 8/2012 | Eyrard ................ A61M 1/1656 137/1 |
| 2013/0001165 A1 | 1/2013 | Pohlmeier |
| 2013/0015302 A1 | 1/2013 | Orter et al. |
| 2013/0062265 A1 | 3/2013 | Balschat |
| 2014/0018727 A1 | 1/2014 | Burbank |
| 2014/0238940 A1 | 8/2014 | Schwarz |
| 2017/0021076 A1 | 1/2017 | Lura |
| 2017/0021086 A1 | 1/2017 | Lura |

FOREIGN PATENT DOCUMENTS

| | | |
|---|---|---|
| WO | WO2000057935 A1 | 10/2000 |
| WO | WO 2013077844 | 5/2013 |
| WO | WO 2017004449 | 1/2017 |

OTHER PUBLICATIONS

[NPL638] Written Opinion, Application PCT/US2016/043935, dated Feb. 2, 2017.
Int'l Search Report PCT/US217/032337.
PCT/US2017/025868 International Search Report dated Jun. 29, 2017.
PCTUS2017025858 International Search Report dated Jun. 29, 2017.
PCTUS2017025858 Written Opinion dated Jun. 29, 2017.
PCTUS2017025876 International Search Report dated Jun. 29, 2017.
PCTUS2017025876 Written Opinion dated Jun. 29, 2017.

* cited by examiner

INFUSATE CONTAINERS

FIELD OF THE INVENTION

The invention relates to infusate containers and related systems and methods for housing infusates that can be added to a fluid flow path for use during dialysis. The infusate containers can include a filter partitioning the containers into a first and second compartment, a draw tube for drawing up fluid from a bottom portion, a cap, a fluid connector for delivery and withdrawal of fluid from the two compartments, and a fluid connector for connection to a dialysis system.

BACKGROUND

During priming of a dialysis system and during dialysis treatment, specific concentrations of specific solutions, such as sodium chloride, sodium bicarbonate, and cation infusates, must be added to the dialysate flow path. Further, many cations, such as potassium, calcium and magnesium, can cross the dialyzer and be removed from a patient during dialysis. The cations must be added back into the dialysate to maintain the concentration of the cations at a desired level. Sodium bicarbonate can be used during dialysis as a buffer to control the pH of the dialysate and to treat acidosis by delivering bicarbonate across the dialysis membrane to the patient receiving a treatment. The amounts of sodium chloride, sodium bicarbonate and other cations added to dialysate should be closely monitored and controlled. Further, the amounts of each of the solutions necessary can vary considerably.

There is a need for infusate containers that ensure proper solutes are added in proper amounts to the dialysate. There is a need for infusate containers that allow solid infusate sources to be dissolved, creating infusate solutions of known concentration while preventing any particulate matter from entering the dialysis system. To facilitate use of dialysis by personnel, systems and methods are needed that can ensure that any of the solutes or solutions are properly added to the dialysis system. Further, systems and methods are needed to ensure that all necessary components to be used during dialysis are connected to the dialysis system at the correct locations for a dialysate flow path. There is also a need for low cost, easily manufactured, and low cost housing for mixing and delivering infusates for use during dialysis.

SUMMARY OF THE INVENTION

The first aspect of the invention relates to an infusate container for use in dialysis. In any embodiment, the infusate container can include a container body; a cap removably connected to a top portion of the container body; the cap having a fluid connector for connection to a dialysis system; a draw tube downwardly extending through the container body; the draw tube connected to the cap; and a filter connected to the container body; the filter separating the container body into the top portion and a bottom portion; the draw tube downwardly extending through the filter into the bottom portion.

In any embodiment, the infusate container can include an inwardly tapering portion in the bottom portion of the infusate container.

In any embodiment, the infusate container can include a removable film on a top side of the cap.

In any embodiment, the filter can be connected to the container body by any of glue, heat sealing, or welding.

In any embodiment, the filter can be either a mesh or frit filter.

In any embodiment, the connector can be a bi-channel connector.

In any embodiment, the bi-channel connector can have a first channel fluidly connected to the draw tube.

In any embodiment, the infusate container can have a visual indicator indicating a substance inside the container body.

In any embodiment, the visual indicator can be a colored band.

In any embodiment, the draw tube can be molded to the cap.

In any embodiment, the infusate container can have at least one support member, a first end of the support member connected to the draw tube and a second end of the support member in contact with the container body.

Any of the features disclosed as being part of the first aspect of the invention can be included in the first aspect of the invention, either alone or in combination.

The second aspect of the invention is drawn to a dialysis system. In any embodiment, the dialysis system can include a dialysis machine having (i) a dialysate flow path; (ii) one or more fluid connectors fluidly connecting one or more infusate containers of the first aspect of the invention to the dialysate flow path; and (iii) at least one pump connected to a fluid line fluidly connected to the fluid connectors.

In any embodiment, the fluid connector can be a bi-channel connector.

In any embodiment, the infusate container can contain sodium chloride, sodium bicarbonate, a cation infusate, or combinations thereof.

In any embodiment, a first channel of the bi-channel connector can fluidly connect the draw tube to a first fluid line; and a second channel of the bi-channel connector can fluidly connect the infusate container to a second fluid line.

In any embodiment, the dialysis system can include an infusate frame, the infusate frame housing the infusate containers.

In any embodiment, the infusate frame can have one or more apertures for housing the infusate containers; the one or more apertures sized or shaped complementary to the infusate container.

Any of the features disclosed as being part of the second aspect of the invention can be included in the second aspect of the invention, either alone or in combination.

The third aspect of the invention is drawn to a method. In any embodiment, the method can include flowing water into the infusate container the first aspect of the invention, wherein the infusate container contains a solid infusate; dissolving at least a portion of the solid infusate to make an infusate solution; and flowing the infusate solution into a dialysate flow path.

In any embodiment, the step of flowing water into the infusate container can include flowing water through a first channel of a bi-channel connector; and the step of flowing the infusate solution into the dialysate flow path can include flowing the infusate solution through a second channel of the bi-channel connector.

In any embodiment, the step of dissolving at least a portion of the solid infusate to make an infusate solution can include making a saturated infusate solution.

In any embodiment, the infusate can be sodium bicarbonate, sodium chloride, a cation infusate, or a combination thereof.

Any of the features disclosed as being part of the third aspect of the invention can be included in the third aspect of the invention, either alone or in combination.

DETAILED DESCRIPTION OF THE INVENTION

Figure 1:
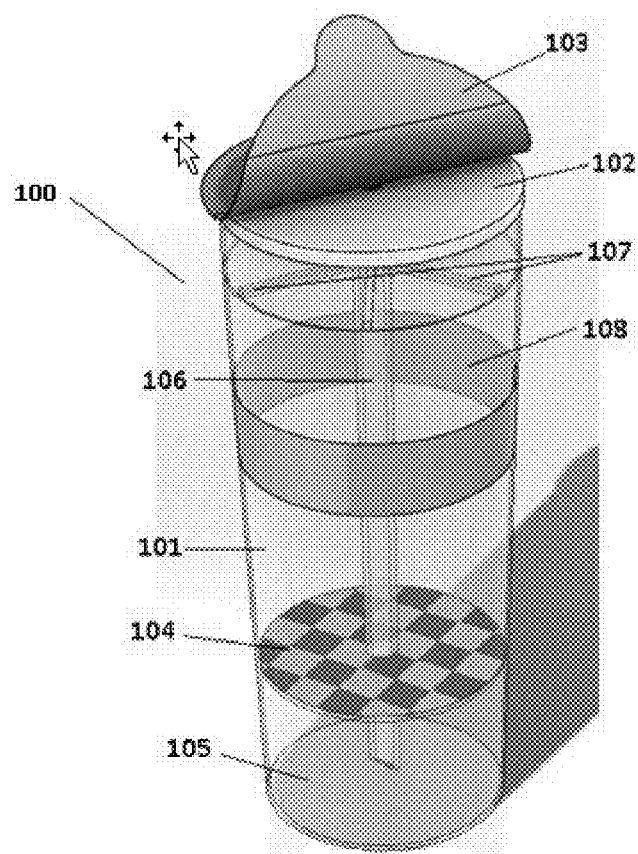
FIG. 1 shows an infusate container for use in a dialysis system.

Unless defined otherwise, all technical and scientific terms used herein generally have the same meaning as commonly understood by one of ordinary skill in the relevant art.

The articles "a" and "an" are used to refer to one or to over one (i.e., to at least one) of the grammatical object of the article. For example, "an element" means one element or over one element.

An "aperture" is a portion of a component having a defined void space. As used in the invention, an aperture in an infusate frame refers to a void space or an opening or slot without any restriction as to size or shape into which an infusate container can be inserted.

The term "bi-channel connector" refers to a fluid connector having two channels for movement of fluid, gas, or mixtures of fluid/gas in either direction in each of the channels.

The term "bottom portion" of a container refers to the portion of the container near or at a lowest elevation.

The term "cap" refers to a portion of a component covering an aperture.

The term "cation infusate" refers to cations added to a dialysate during dialysis therapy.

The term "cation infusate container" refers to a source from which cations can be obtained. Examples of cations include, but are not limited to, calcium, magnesium and potassium. The source can be a solution containing cations or dry compositions hydrated by the system. The cation infusate container is not limited to cations and may optionally include other substances to be infused into a dialysate or replacement fluid; non-limiting examples can include glucose, dextrose, acetic acid and citric acid.

The term "channel" refers to any pathway within a component through which a fluid, gas, mixtures of fluid and gas, a slurry, or any material having sufficient flowability properties to permit travel of the material along the pathway.

The term "colored band" refers to any portion of a container or component having a specific color and/or marking serving as a visual indicator.

The term "complementary," as used to describe fitting features, refers to one or more fitting features on a first component designed to pair or mate with one or more fitting features on a second component. For example, a first component may have a receiving compartment of particular dimensions, and the second component may be the same dimensions, such that the second component can mate within the receiving compartment.

The term "comprising," "comprises," "comprise," and the like includes, but is not limited to, whatever follows the word "comprising." Use of the term indicates the listed elements are required or mandatory but that other elements are optional and may be present.

The terms "connect" or "connected" refer to a physical contact between two components.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "container body" refers to the outer boundaries of a container enclosing an interior of the container.

A "dialysate flow path" is a route in which a fluid can travel during dialysis.

"Dialysis" or "dialysis therapy" is a type of filtration, and/or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis machine" or "dialysis system" is a system and related components having a dialyzer, pumps, valves and fluid lines used to carry out a dialysis session.

The terms "dissolving" or to "dissolve" refer to causing a solid or gas to become incorporated into a liquid to form a solution.

"Downwardly extending" or to "extend downwardly" refers to a component positioned from a higher elevation to a lower elevation.

A "draw tube" is a passageway that can extend into a defined space such as an interior space of a container. The passageway can permit a flow of fluid, gas, mixtures of fluid and gas, a slurry, or any material having sufficient flowability properties to permit travel of the material along the pathway.

A "filter" is a component that inhibits the passage of desired size of particulate matter conveyed by a fluid or solution while allowing the passage of the fluid or solution.

The terms "flowing" or to "flow" refer to the movement of a fluid, gas, mixtures thereof, a slurry, or any material having sufficient flowability properties to permit travel of the material.

A "fluid" is a liquid substance optionally having a combination of gas and liquid phases in the fluid. Notably, a liquid can therefore also have a mixture of gas and liquid phases of matter.

The term "fluid connector," "fluid connectors," "fluidly connectable," or "fluidly connected" refers to a structure, passageway, or ability to pass fluid, gas, or mixtures thereof from one point to another point. The two points can be within or between any one or more of compartments, modules, systems, and components.

The term "fluid line" refers to a fluid pathway.

The term "fluid pump" or "pump" refers to any device that causes the movement of fluids or gases by applying suction or pressure.

The term "frit filter" refers to porous glass made by sintering together glass particles into a porous body.

The term "glue" refers to any adhesive substance capable of holding two components in contact.

The term "heat sealing" refers to the use of heat to unite or connect two thermoplastic materials.

An "infusate container" or "infusate containers" can be a container(s) adapted to contain one or more fluids for dialysis. The infusate container can house dry chemicals that can be later reconstituted with a fluid to form a slurry, mixture, solution, fluid, or material of having sufficient flowability properties to permit travel of the material along a pathway.

An "infusate solution" is any substance or substances dissolved in water or dialysate to be added to a dialysate flow path.

An "infusate frame" is a component detachably removable from a dialysis system having a substantially planar shape, configured to house or receive one or more containers.

The term "inwardly tapered" refers to a three-dimensional part of a component that gradually extends towards a point when moving from the outside of the component to the inside of the component.

The term "mesh" refers to a component made of strands of fibers with spaces between the fibers to allow fluid or gas to flow through the mesh.

The term "molded" refers to forming a component having a particular shape from a larger or unshaped substance.

The terms "removable," "removed," or "removably connected" relate to any component of the present invention that can be separated from a system, module, cartridge or any component of the invention.

The term "removable film" refers to a covering or coating on a component that can be separated from the component.

The term "saturated" refers to the highest amount of a substance that can be dissolved in a solvent at a given temperature.

"Shape" can refer to a two or three dimensional form of a component. For example, the shape of an substantially two dimensional aperture can be circular, rectangular, square, trapezoidal, or any other geometric shape. In reference to a three dimensional form, the shape of a container can be cylindrical, cube, spherical, cone, or any other known volumetric shape.

"Size" can refer to the area, surface area, or volume of a container or component.

The terms "sodium bicarbonate container" refers to an object that can be a stand-alone enclosure or alternatively can be integrally formed with an apparatus for hemodialysis, hemodiafiltration, or hemofiltration. The object can store a source of sodium bicarbonate in solid and/or solution form, and can be configured to interface with at least one other functional module found in systems for hemodialysis, hemodiafiltration, or hemofiltration. The sodium bicarbonate reservoir or container can contain at least one fluid pathway and include components such as conduits, valves, filters or fluid connection ports.

The terms "sodium chloride container" refers to an object that can be a stand-alone enclosure or alternatively can be integrally formed with an apparatus for hemodialysis, hemodiafiltration, or hemofiltration. The object can store a source of sodium, such as sodium chloride in solid and/or solution form, and can be configured to interface with at least one other functional module found in systems for hemodialysis, hemodiafiltration, or hemofiltration. The sodium chloride reservoir or container can contain at least one fluid pathway and include components such as conduits, valves, filters or fluid connection ports.

The term "solid infusate" refers to any substance intended to be added to a dialysate flow path in the solid form of matter.

A "support member" is any structure connected to a component designed to hold or rigidly affix the component in a particular location, configuration, or orientation.

The term "top portion" of a container refers to the portion of the container near or at a highest elevation.

A "visual indicator" is any visible indication of a particular position for a component or substance. The visual indicator can be a color coding system, a label, or any other system that informs a user of an intended position for a component or substance.

The term "welding" refers to the process of connecting two components by heating at least one component to or above the melting point and uniting the components by pressure.

Infusate Containers

The infusate containers of the present invention can include a filter partitioning the container into a top and bottom compartment and having a draw tube for drawing up fluid from the bottom compartment, which is partitioned from the top portion by the filter. One or more fluid connectors can be positioned at the top of the infusate container to deliver a fluid directly into the top compartment containing an infusate material to dissolve the material into the top compartment. The liquefied material, solution, or slurry in the top compartment can then be filtered by the filter and pass into the bottom compartment by gravity where the resulting solution can be drawn by the draw tube up and into the one or more fluid connectors. FIG. 1 illustrates a non-limiting embodiment of an infusate container 100. The infusate container 100 has a container body 101 defining a space into which infusates can be housed for use in dialysis. The infusates can be in a solid, a slurry, or solution form. For use with solid infusates, water can be added to the infusate container 100 to dissolve the infusate into a slurry or solution, making a slurry or solution of known concentration for addition to a dialysis system. For example, an excess amount of the solid infusate can be added to the infusate container 100. Water can then be added to the infusate container 100 in an amount insufficient to dissolve all of the solid infusate. The resulting infusate solution will be saturated in the infusate. At known temperatures, the concentration of the infusate in the saturated infusate solution will be known. Alternatively, a specified amount of solid infusate and water can be added to the infusate container 100 to generate an infusate solution of known concentration. A cap 102 can cover the infusate container 100 during use. The cap 102 can be detached from the container body 101 to facilitate addition of infusates into the infusate container 100. A protective removable film 103 can cover the cap 102 prior to use, maintaining the sterility of the cap 102. The removable film can be tear-off type having any suitable configuration to ensure the sterility of the cap 102.

For use with solid infusates, a filter 104 can be included above the base 105 of the infusate container 100, separating the infusate container 100 into top and bottom portions. The solid infusate can be placed on top of the filter 104. Water can be added to dissolve the infusate with the resulting solution flowing through the filter 104 into the bottom portion. The solids can be prevented from passing through the filter 104, and remain in the top portion. The filter 104 can be any type of filter known in the art capable of preventing solid or particulate matter from passing through the filter 104, including a frit filter or a mesh filter. The filter 104 can be connected to the container body 101 by any method known in the art. The filter 104 can be glued, welded, or heat sealed to the container body 101. A draw tube 106 can extend downwardly from the cap 102 through the filter 104. The solution in the bottom portion of the infusate container 100 can be drawn through the draw tube 106 and added to a dialysate flow path with a pump positioned on a fluid line connected to the draw tube 106.

The infusate container 100 can include optional support members 107 and be constructed by blow molding, injection, or other suitable process. The components can be assembled using glue, welding, or any other suitable fabrication technique known to those of skill in the art. Notably, the frit filter or a mesh filter can be inserted during the manufacturing process. The infusate containers of the present invention can be for single-use (disposable) or constructed for multiple use. The support members 107 have a first end connected to the draw tube 106 and a second end in contact with the container body 101. The support members 107 ensure that the draw tube 106 remains properly situated within the container during use. The draw tube 106 can be permanently attached to the cap 102 via molding, gluing, or other known technique. For example the draw tube 106 can be molded to the cap 102. Alternatively, the draw tube 106 can be a separate structure from the cap 102, placed into the infusate container 100 before use.

A visual indicator can be included, the visual indicator indicating the substance contained within the infusate container 100. As illustrated in FIG. 1, the visual indicator can be a colored band 108. Each container having a different infusate can have a different colored band 108. For example, a sodium chloride container can have a green band, while a sodium bicarbonate container can have a red band. Any visual indicator of the substance within the infusate container 100 can be used, including words, letters, or any other indicator of the substance in the container. The visual indicators ensure the correct substances are placed in the correct containers. A second visual indicator can be included on the connectors from the dialysis system (not shown in FIG. 1). For example, the sodium chloride container can have a green colored band 108, and a connector 203 as shown in FIG. 23 used for connection to the sodium chloride container can be colored green.

Figure 2:
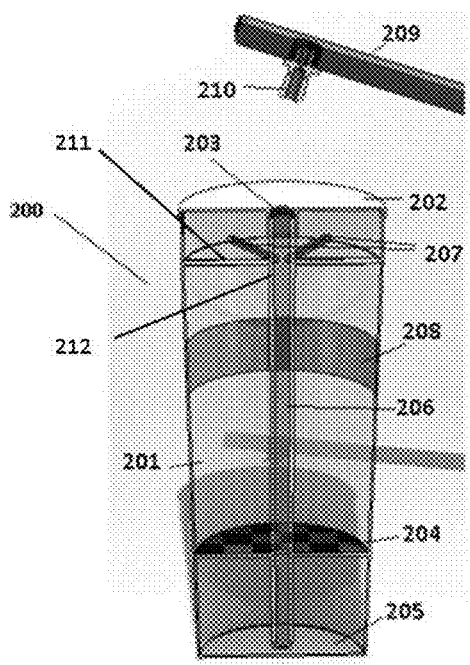
FIG. 2 shows an infusate container being connected to a dialysis system.

FIG. 2 illustrates an infusate container 200 for connection to a dialysis system. The infusate container 200 includes container body 201 and cap 202. A draw tube 206 extends downwardly from the cap 202 through a filter 204. The draw tube 206 includes a connector 203 for connection to the dialysis system, and optional support members 207 to support the draw tube 206. The connector 203 can be a socket type port for quick connection complementary to any other suitable connection to ensure a sealably connected fit. A corresponding dialysis machine connector 210 can be fluidly connected to the dialysis system for movement of fluid to and from the infusate container 200. The dialysis machine connector 210 can be fluidly connected to a fluid line, the fluid line fluidly connecting to a dialysate flow path. In FIG. 2, the dialysis machine connector 210 is shown on a cantilevered paddle 209. The cantilevered paddle 209 can be moved downward to engage the infusate container connector 203 and dialysis machine connector 210. To further resist the downward force of the cantilevered paddle 209, the support members 207 can rest on an optional surface 211. The surface 211 can have a hole 212 positioned at the center of the surface 211 to allow the draw tube 206 to pass through. The support members 207 ensure that a bottom end of the draw tube 206 in the portion below the filter 204 does not contact the base 205 so that fluid can be sufficiently drawn 206 back into the draw tube 206. Other connections between the infusate container 200 and the dialysis machine can be used, including a length of hose, or any other connection. The infusate container connector 203 and dialysis machine connector 210 can be selected from a range of connectors known in the art. One non-limiting example is a quick-connect connector available from LinkTech, a California corporation. The quick-connect connector engages by snapping male and female portions of the connector together, forming a fluid connection. However, a useful type of connector known in the art can be selected.

A solid infusate source, such as solid sodium chloride, or any other suitable infusate for dialysis such as bicarbonate can be placed in the infusate container 200 above the filter 204. A visual indicator, such as colored band 208, can provide quick and easy visual indication of whether the proper infusate source has been added in the infusate container 200 and is being properly used during operation. The infusate container 200 can be connected to the dialysis machine through container connector 203 and dialysis machine connector 210. Purified water from the dialysis machine can be flowed into the infusate container 200, dissolving the solid infusate source contained in a space above the filter 204. The connector 203 can have a two channels such that a first channel delivers the purified water directly into the space above the filter 204 and a second channel is connected to the drawtube. In this manner, the resulting solution in the portion above the filter 204 can pass through the filter 204 and into the bottom section of the infusate container 200 above base 205. The infusate solution can be flowed out of the infusate container 200 through draw tube 206, container connector 203, and dialysis machine connector 210.

Figure 3:
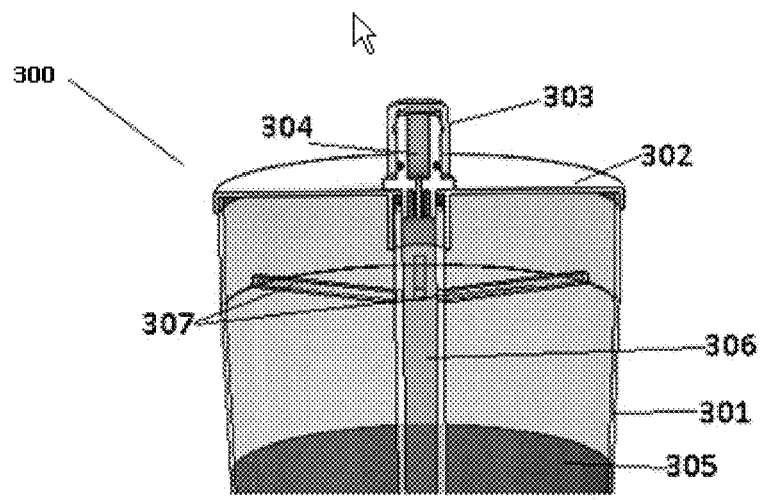
FIG. 3 is a close-up view of the top of an infusate container.

FIG. 3 shows a close-up view of the top of an infusate container 300. The infusate container 300 includes a chamber body 301, cap 302, and a draw tube 306 downwardly extending through a filter above a base (not shown in FIG. 3) of the infusate container 300. Support members 307 can be included to support the draw tube 306. A container connector 303 connects to the draw tube 306 through the cap 302. The container connector 303 includes at least one channel 304 for the movement of fluid into and out of the infusate container 300. Colored band 305 or other visual indicator indicates the substance intended to be placed in the infusate container 300.

Figure 4:
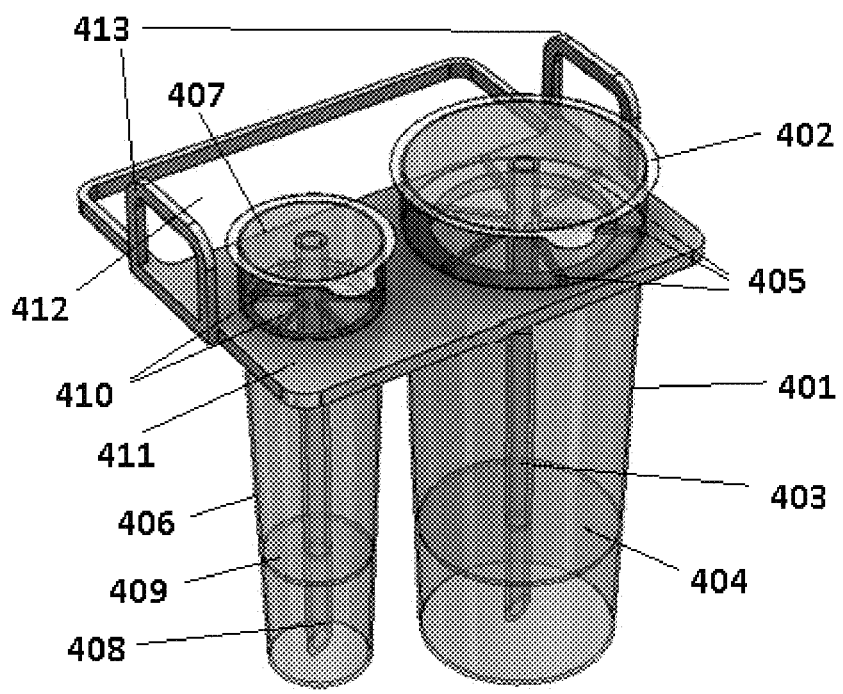
FIG. 4 shows infusate containers seated in an infusate frame.

The infusate frame can be configured to house or receive any number of infusate containers. For example, an infusate frame can house one infusate container, two infusate containers, three infusate containers, or more. Each infusate container can contain the same or different infusate materials for use in dialysis. Each of the infusate containers can be removably positioned in the infusate frame with each infusate container shaped in a particular size, shape, or diameter. The infusate containers can be shaped the same or different from each other. In one non-limiting embodiment, FIG. 4 shows an infusate frame 411 receiving two infusate containers. The infusate frame 411 can include one or more openings, apertures, or receiving slots of numerous size and shapes adapted to receive the infusate containers. A cylindrically shaped sodium bicarbonate container 401 having downward taper can have a cap 402, a draw tube 403, and a filter 404. The cylindrically shaped sodium bicarbonate container 401 can have a first diameter along the tapered length corresponding to a first aperture 414 on the infusate frame 411. The first aperture 414 on the infusate frame 411 can be suitably sized to receive the sodium bicarbonate container 401. Solid sodium bicarbonate can be placed in the sodium bicarbonate container 401 above filter 404. The draw tube 403 can be positioned concentric to the cylindrically shaped sodium bicarbonate container 401 and supported by support members 405. A sodium chloride container can have a container body 406, cap 407, draw tube 408, and filter 409. The draw tube 408 can be supported by support members 410. Solid sodium chloride can be placed in the container above filter 409. The infusate frame 411 can also include a third aperture 412 shaped in a rectangular form for receiving an additional infusate container (not shown in FIG. 4), such as a cation infusate container. Many types of apertures can be included in the infusate frame 411 for receiving infusate containers.

The infusate frame 411 can be inserted into a receiving compartment of a dialysis machine (not shown), placing the infusate containers in alignment with dialysis machine connectors for connection to a dialysate flow path. The apertures in the infusate frame 411 can be sized and shaped complementary to the size and shape of the infusate containers. For example, as illustrated in FIG. 4, the sodium bicarbonate container 401 can have a container body with a larger radius than the container body 406 of the sodium chloride container. The sodium bicarbonate container 401 cannot fit within the aperture for the sodium chloride container and vice versa. When inserted into a receiving compartment of a dialysis machine, the larger aperture can be aligned with a dialysis machine connector for sodium bicarbonate, while the smaller aperture can be aligned with a dialysis machine connector for sodium chloride, ensuring that the proper solutes are added to the dialysate flow path at the proper locations and in the proper amounts.

Figure 5A:
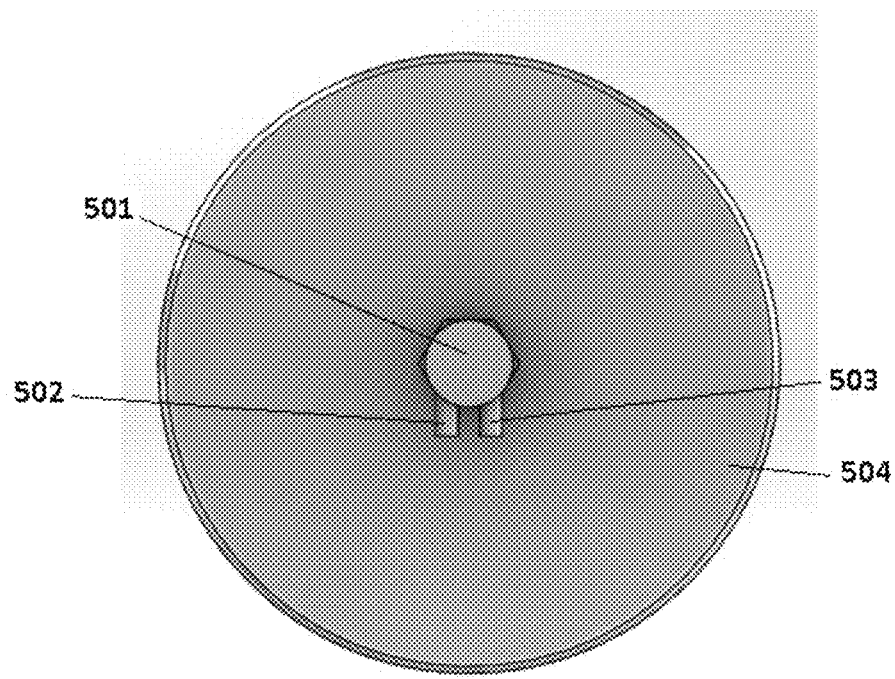
FIGS. 5A-D show bi-channel connectors for use with the infusate containers.
Figure 5B:
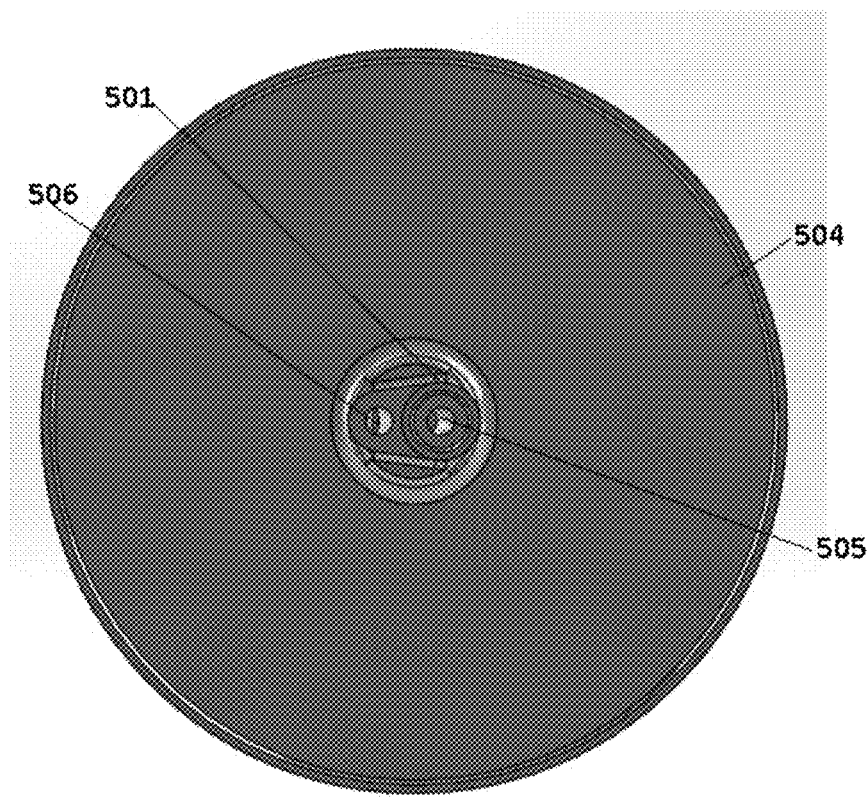
Figure 5C:
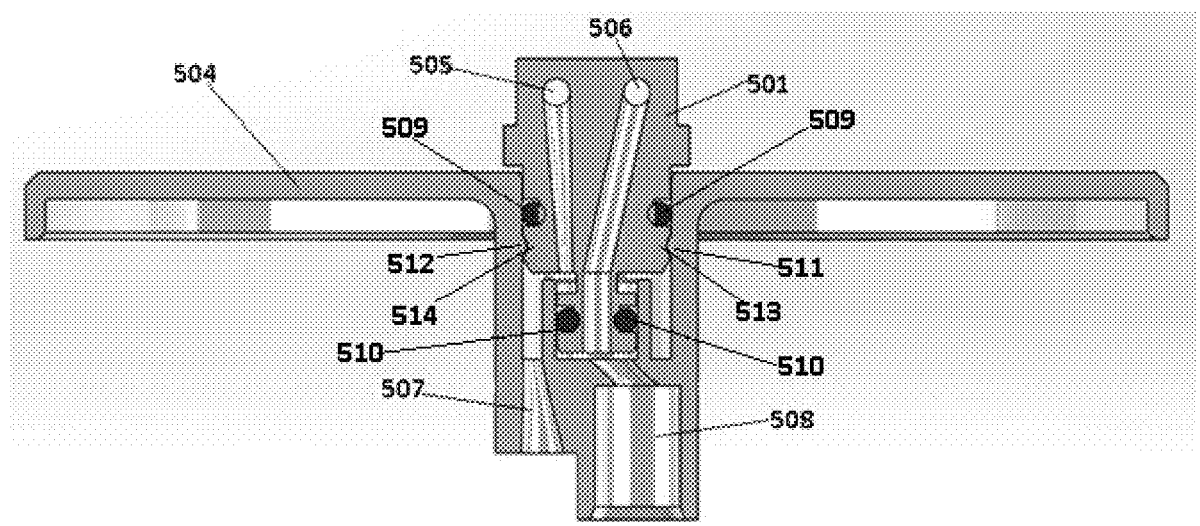
Figure 5D:
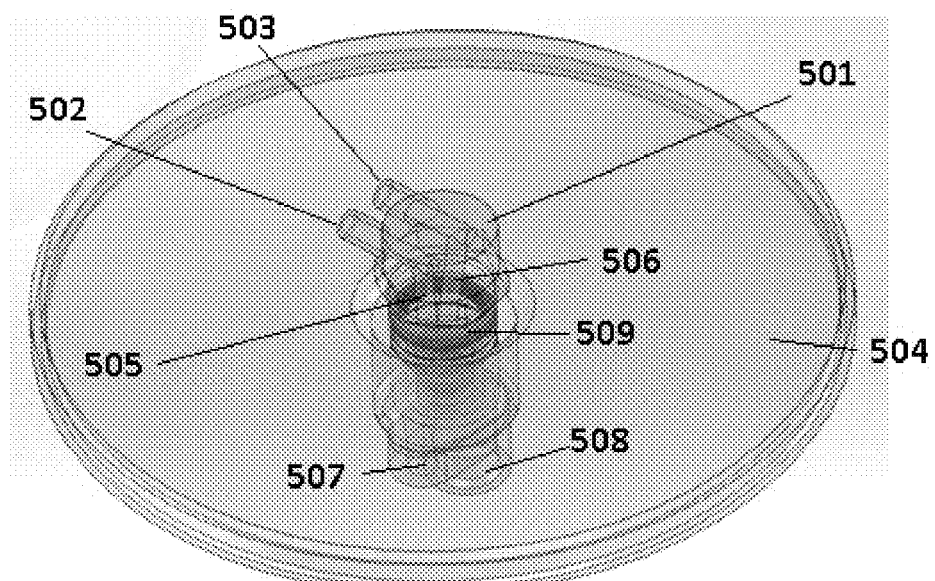

Any of the connectors described can be bi-channel connectors. FIGS. 5A-D illustrate one embodiment of a bi-channel connector. FIG. 5A is a top view of a bi-channel connector 501, FIG. 5B is a top cut-away view of the bi-channel connector, FIG. 5C is a cross-sectional view of the bi-channel connector 501, and FIG. 5D is a transparent view of the bi-channel connector 501. Each view shows an infusate container cap 504 and bi-channel connector 501. The bi-channel connector 501 includes fluid inlet 502 for moving fluid into the infusate container 500, and fluid outlet 503 for removing fluid from the infusate container 500. The fluid inlet 502 is connected to a first channel 505, and the fluid outlet 503 is connected to a second channel 506, as illustrated in FIG. 5B. The first channel 505 is connected to a container inlet 507 for movement of fluid into the infusate container 500. The second channel 506 is connected to container outlet 508 for movement of fluid out of the infusate container 500. The container outlet 508 can be connected to a draw tube (not shown in FIGS. 5A-D) that extends downwardly into the infusate container 500. An o-ring or other sealing member 509 can be included to prevent leakage around the cap 504 of the infusate container 500 where the cap 504 contacts the bi-channel connector 501. As illustrated in FIG. 5C, a second o-ring 510 can be included to prevent leakage between the first channel 505 and second channel 506. The container cap 504 can also include protrusions 511 and 512 which can engage with complementary indentations 513 and 514 on the bi-channel connector 501 to securely fasten the bi-channel connector 501 in place on the container cap 504 without the need to twist or screw the bi-channel connector 501.

The fluid inlet 502 and fluid outlet 503 can be connected to a dialysis system through separate fluid lines. By using separate fluid lines for influx and efflux of fluid to and from the infusate container 500, additional water can be added to the infusate container 500 during priming or use without contamination of the infusates within the container.

Figure 6:
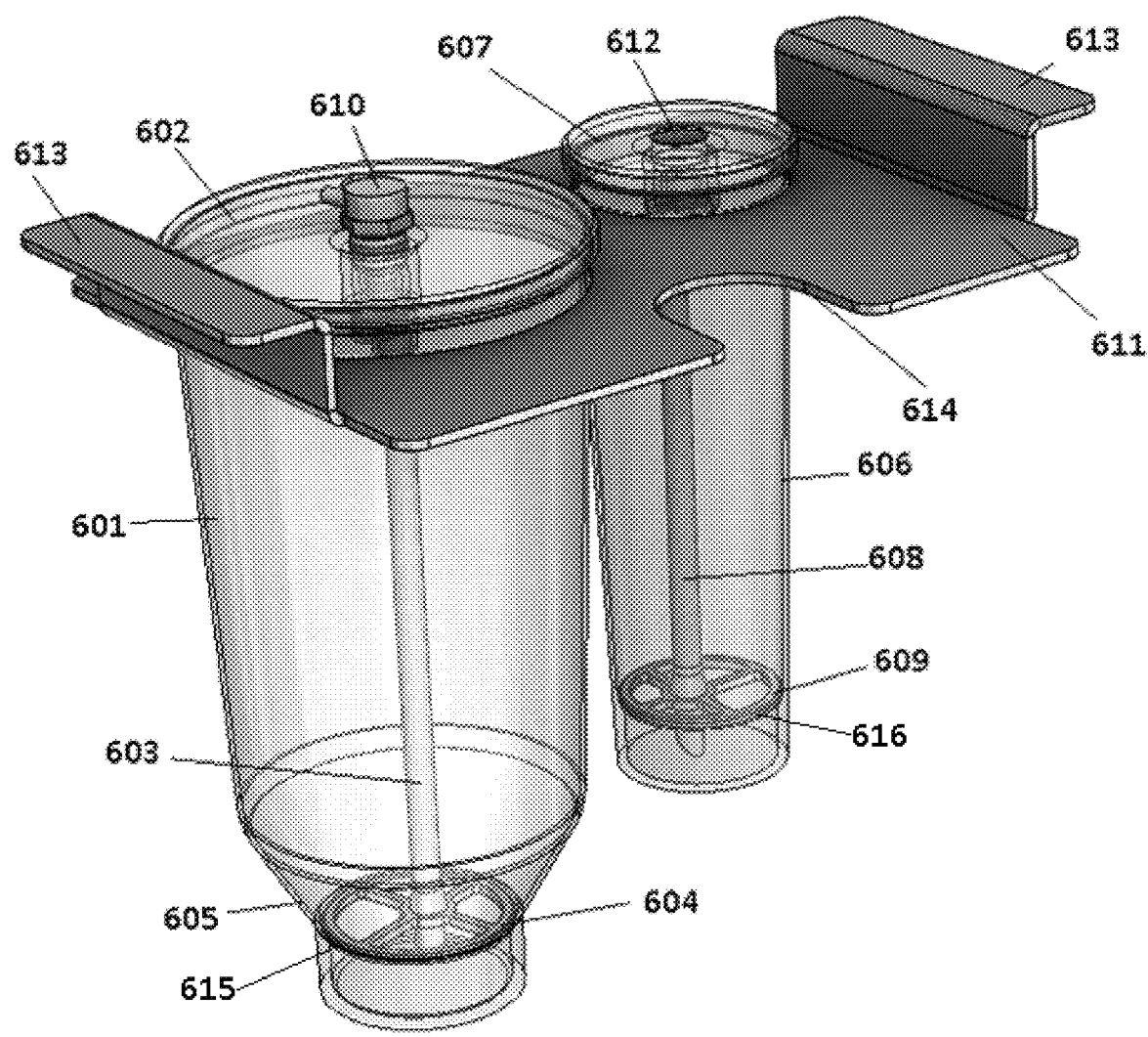
FIG. 6 shows infusate containers seated in an infusate frame.

FIG. 6 illustrates an infusate frame 611 for receiving three infusate containers. A sodium bicarbonate container 601 having downward taper in bottom portion 605 can have a cap 602, a draw tube 603, and a filter 604. The sodium bicarbonate container 601 can have a first diameter along the tapered length corresponding to a first aperture on the infusate frame 611. The first aperture on the infusate frame 611 can be suitably sized to receive the sodium bicarbonate container 601. Solid sodium bicarbonate can be placed in the sodium bicarbonate container 601 above filter 604. An o-ring 615 can be included around the filter 604 in sodium bicarbonate container 601 and a second o-ring 616 can be included around the filter 609 in sodium chloride container body 606. The o-rings 615 and 616 prevent channeling of fluid around the edges of the filters 604 and 609. The draw tube 603 can be positioned concentric to the sodium bicarbonate container 601 and supported by support members (not shown). Fluid connector 610 can connect the sodium bicarbonate container 601 to a dialysis machine (not shown) when in use. A sodium chloride container can have a container body 606, cap 607, draw tube 608, and filter 609. The draw tube 608 can be supported by support members (not shown). Solid sodium chloride can be placed in the container body 606 above filter 609. Fluid connector 612 can connect the sodium chloride container to a dialysis machine when in use. The infusate frame 611 can also include a third aperture 614 slotted to a periphery of the infusate frame 611 for receiving an additional infusate container (not shown in FIG. 6), such as a cation infusate container. Additional apertures can be included in the infusate frame 611 for additional infusate containers. When inserted into a receiving compartment of a dialysis machine (not shown) support lips 613 can engage with a ledge in the receiving compartment of the dialysis machine, supporting the infusate frame 611.

Figure 7:
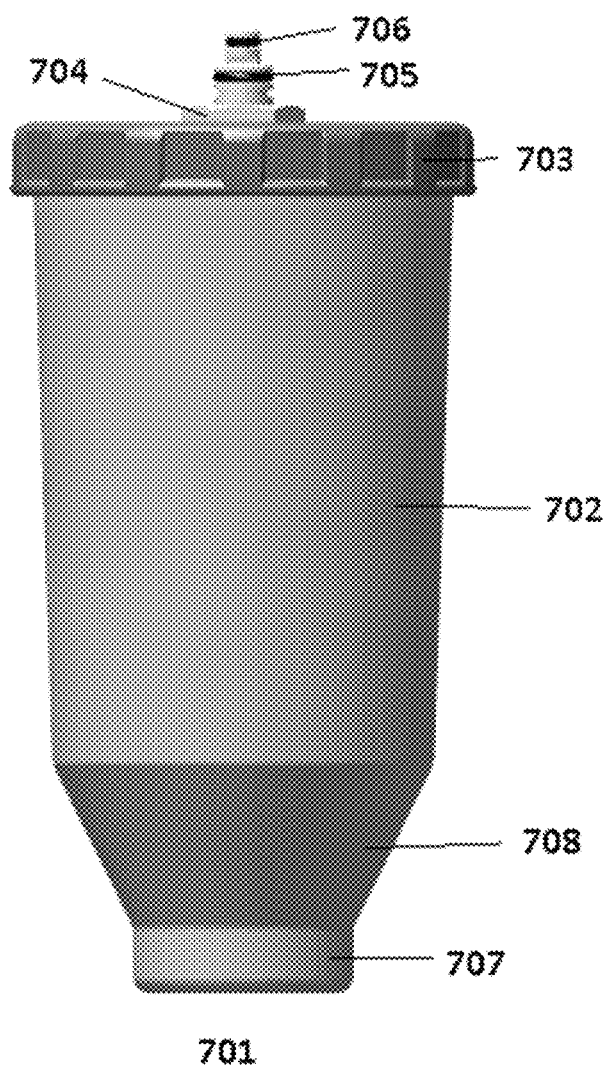
FIG. 7 shows a sodium bicarbonate infusate container.

FIG. 7 illustrates a sodium bicarbonate container 701 having a container body 702 and connected to a cap 703. A fluid connector 704 can extend through the cap 703 and connect to a draw tube (not shown). The fluid connector 704 can be a bi-channel connector, and can include o-rings 705 and 706 to form seals around dialysis machine connectors when the sodium bicarbonate container 701 is connected to a dialysis system (not shown). The container body 702 can include a tapered portion 708 tapering inwardly towards a base 707 of the container body 702, increasing the efficiency of sodium bicarbonate delivery. A filter (not shown) can be included in the container body 702, at or below the tapered portion 708.

Experiment 1

Figure 8:
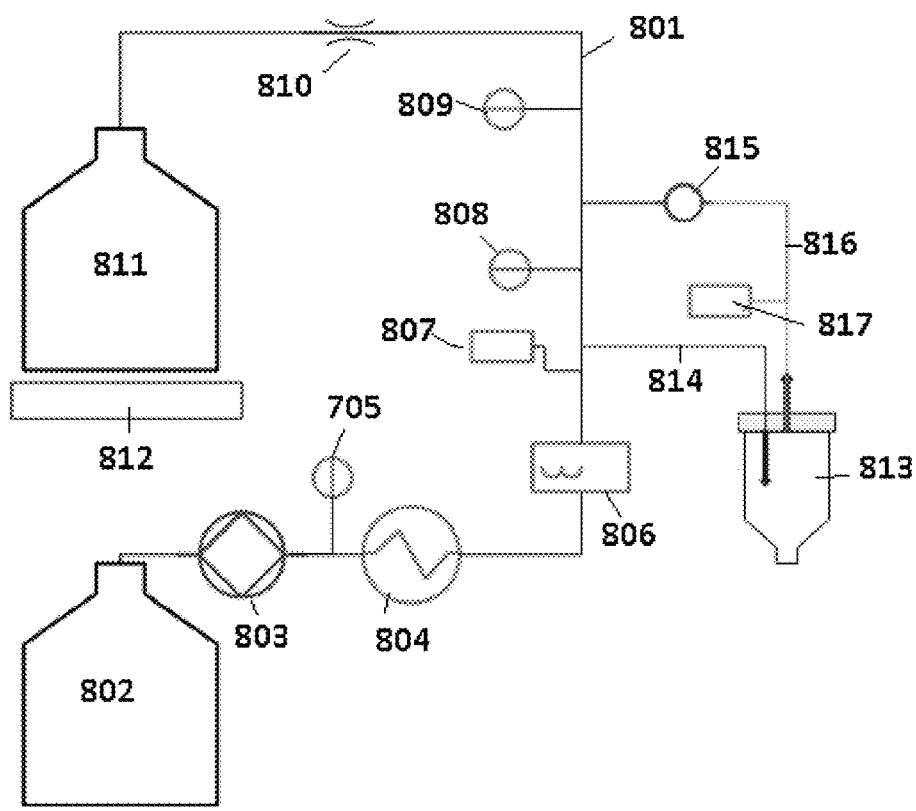
FIG. 8 shows an experimental setup to test the delivery efficiency of sodium bicarbonate from the sodium bicarbonate container.

The tapered portion 708 at the bottom of the sodium bicarbonate container 702 increases efficiency in dissolving and delivering sodium bicarbonate to the dialysis system. FIG. 8 illustrates the experimental setup for measuring the efficiency of sodium bicarbonate delivery. A dialysate source 802 is connected to a dialysate flow path 801. Dialysate pump 803 moves the dialysate from the dialysate source 802 through the dialysate flow path 801 to a drain 811. Heater 804 heats the dialysate to a desired temperature. Flow meter 805 measures the flow rate of fluid in the dialysate flow path 801. Pressure sensor 807 measures the pressure in the dialysate flow path 801. Conductivity sensor 808 measures the dialysate conductivity prior to addition of sodium bicarbonate, and conductivity sensor 809 measures the dialysate conductivity after addition of sodium bicarbonate. Flow scale 812 measures the mass of the liquid flowed into the drain 811. Dialysate is flowed into the sodium bicarbonate container 813 through inlet line 814. Metering pump 815 controls the movement of fluid from the sodium bicarbonate container 813 into the outlet line 816. Pressure sensor 817 measures the fluid pressure in the outlet line 816.

In each experiment, the sodium bicarbonate container 813 was filled with solid sodium bicarbonate up to the level of the support members, as illustrated in FIGS. 1-4. Sodium bicarbonate was obtained from three different sources, Fisher Scientific, a Pennsylvania corporation; Bellco, an Italian corporation; and Koncen, a Chinese corporation. Table 1 illustrates the mass yield of bicarbonate obtained from the sodium bicarbonate container 813.

TABLE 1

| RUN | Material | Filling Mass | Delivered Mass Yield | Yield % |
|---|---|---|---|---|
| 1 | Fisher Scientific | 394 | 362 | 91 |
| 2 | Fisher Scientific | 394 | 359 | 91 |
| 3 | Fisher Scientific | 394 | 368 | 93 |
| 4 | Fisher Scientific | 482 | 465 | 96 |
| 5 | Bellco | 531 | 503 | 95 |
| 6 | Koncen | 552 | 476* | 86 |

*This run had partial breakthroughs prior to final depletion

As illustrated in Table 1, the sodium bicarbonate from Fisher Scientific and Bellco resulted in greater than 90% yield based on the filling and delivery mass of sodium bicarbonate. The sodium bicarbonate from Koncen resulted in breakthrough prior to depletion of the sodium bicarbonate, possibly due to channeling of fluid. Sodium bicarbonate containers having a non-tapered container body produced mass yields of about 50%.

The concentration of the sodium bicarbonate concentrate obtained from the sodium bicarbonate container 813 was also determined using the conductivity sensors in FIG. 8. At a metering pump 815 set point of 200 mL/min, the actual volumetric flow rate is approximately 185 ml/min, and the concentrate produced is approximately 950 mmol/L, resulting in a mass flow rate of 180 mmol/min with each bicarbonate source tested. At typical treatment bicarbonate metering rates, the expected concentration is as provided in Table 2.

TABLE 2

| Metering Rate (mmol/min) | Concentrate Concentration (mmol/L) |
|---|---|
| 190 | 950 |
| 22 | 1100 |
| 11.5 | 1150 |

Table 3 provides the concentrate concentrations and mass flow rates at each of the metering pump 815 rates.

TABLE 3

| RUN | Material | mmol/Rot at Max Flow Rate | Maximum Mass Flow Rate (mmol/min) | Concentrate Concentration at Max Flow Rate (mmol/L) | Concentrate Concentration at 20 ml/min (mmol/L) | Concentrate Concentration at 10 ml/min (mmol/L) |
|---|---|---|---|---|---|---|
| 1 | Fisher Scientific | 0.59 | 175 | 950 | 1150 | 1190 |
| 2 | Fisher Scientific | 0.59 | 195 | 950 | 1100 | 1190 |
| 3 | Fisher Scientific | 0.59 | 188 | 950 | 1100 | 1200 |
| 4 | Fisher Scientific | 0.58 | 188 | 940 | 1110 | 1180 |
| 5 | Bellco | 0.6 | 182 | 960 | 1110 | 1145 |
| 6 | Koncen | 0.58 | 181 | 930 | 1130 | 1190 |

As illustrated in FIG. 3, the sodium bicarbonate from all three sources concentrate concentrations near the expected concentrate concentrations at all three metering pump 815 rates tested.

Figure 9:
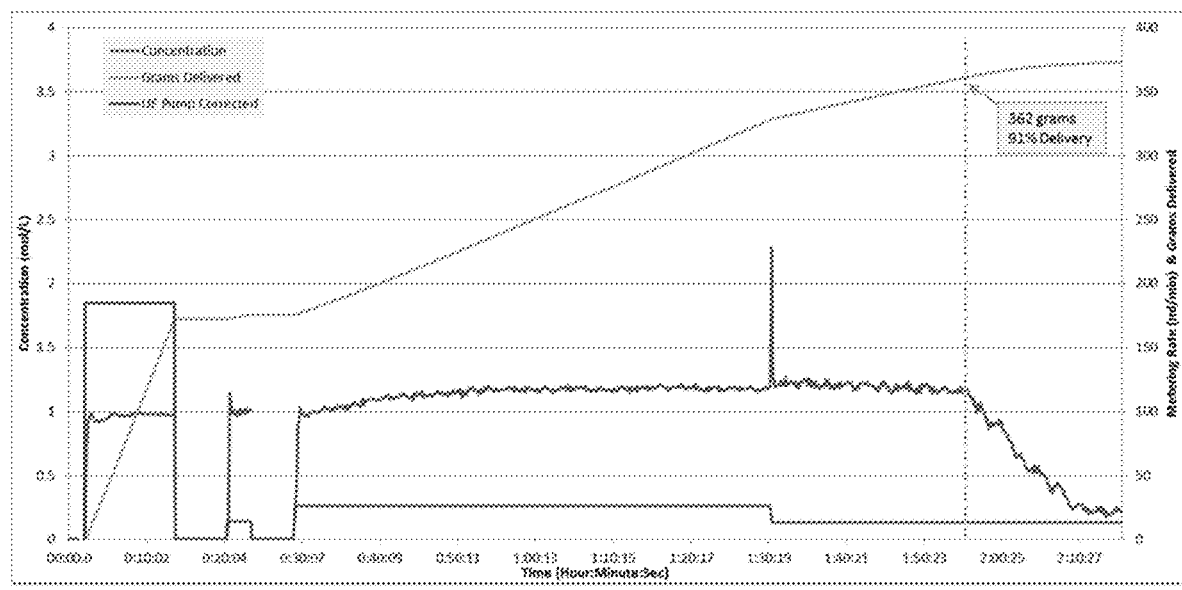
FIG. 9 is a graph showing delivery of sodium bicarbonate from Fisher Scientific using a nominal fill volume.

FIG. 9 is a graph showing the sodium bicarbonate concentrate concentration, the mass of sodium bicarbonate delivered, and the metering pump rate as tested using the Fisher Scientific sodium bicarbonate with a nominal fill volume of 394 g. The top line in FIG. 9 is the total mass of sodium bicarbonate delivered, the center line is the concentration of the sodium bicarbonate, and the bottom line is the metering pump rate. As illustrated in FIG. 9, the concentrate reached at steady concentration after about 13 minutes, and maintained a steady concentration until about 1 hour and 55 minutes, at which point the sodium bicarbonate in the sodium bicarbonate container 813 began to be depleted. The total mass delivered at the point at which the concentration dropped was 362 g, or a 91% delivery efficiency.

Figure 10:
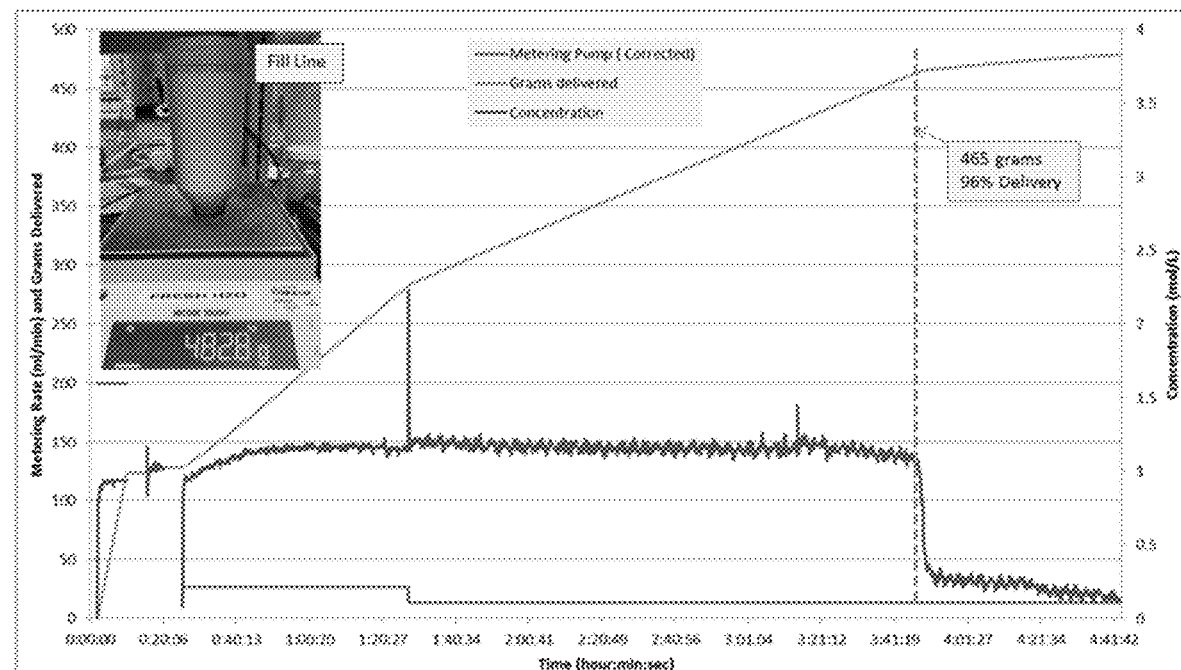
FIG. 10 is a graph showing delivery of sodium bicarbonate from Fisher Scientific using a maximum fill volume.

FIG. 10 is a graph showing the sodium bicarbonate concentrate concentration, the mass of sodium bicarbonate delivered, and the metering pump rate as tested using the Fisher Scientific sodium bicarbonate using a maximum fill volume of 483 g. The top line in FIG. 10 is the total mass of sodium bicarbonate delivered, the center line is the concentration of the sodium bicarbonate, and the bottom line is the metering pump rate. As illustrated in FIG. 10, the concentrate reached at steady concentration after about 30 minutes, and maintained a steady concentration until about 3 hours and 45 minutes, at which point the sodium bicarbonate in the sodium bicarbonate container 813 began to be depleted. The total mass delivered at the point at which the concentration dropped was 465 g, or a 96% delivery efficiency.

Figure 11:
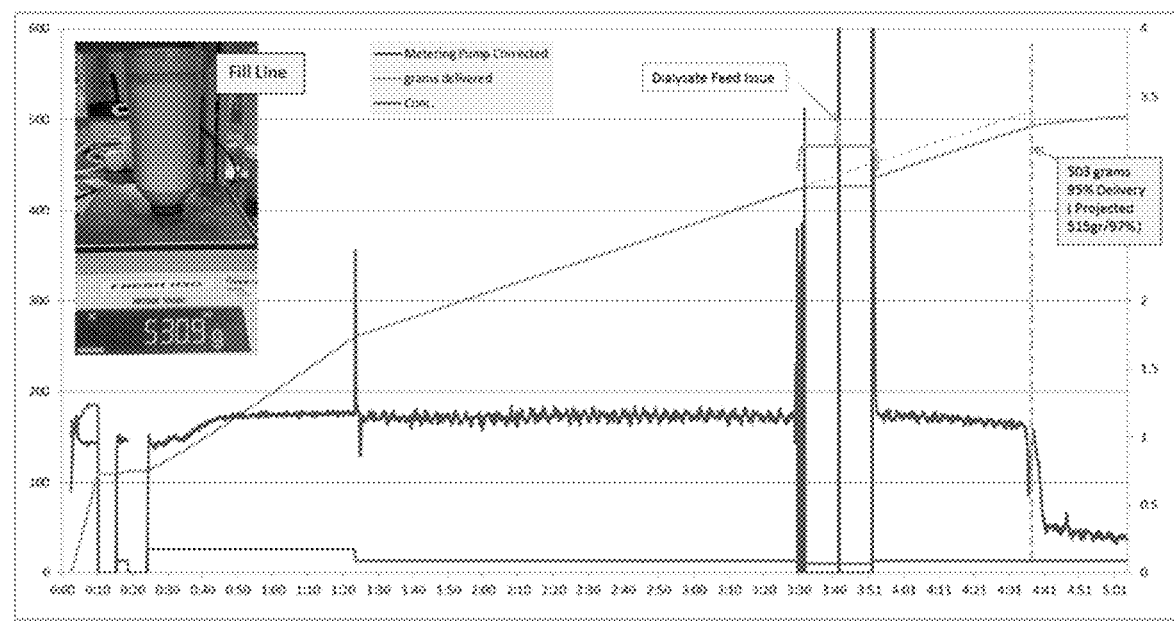
FIG. 11 is a graph showing delivery of sodium bicarbonate from Bellco using a maximum fill volume.

FIG. 11 is a graph showing the sodium bicarbonate concentrate concentration, the mass of sodium bicarbonate delivered, and the metering pump rate as tested using the Bellco sodium bicarbonate using a maximum fill volume of 531 g. The top line in FIG. 11 is the total mass of sodium bicarbonate delivered, the center line is the concentration of the sodium bicarbonate, and the bottom line is the metering pump rate. As illustrated in FIG. 11, the concentrate reached at steady concentration after about 25 minutes, and maintained a steady concentration until about 4 hours and 40 minutes, at which point the sodium bicarbonate in the sodium bicarbonate container 813 began to be depleted, with the exception of the time between 3 hours and 30 minutes and 3 hours and 50 minutes, during which the experimental setup experienced a dialysate feed issue. The total mass delivered at the point at which the concentration dropped was 503 g, or a 95% delivery efficiency.

Figure 12:
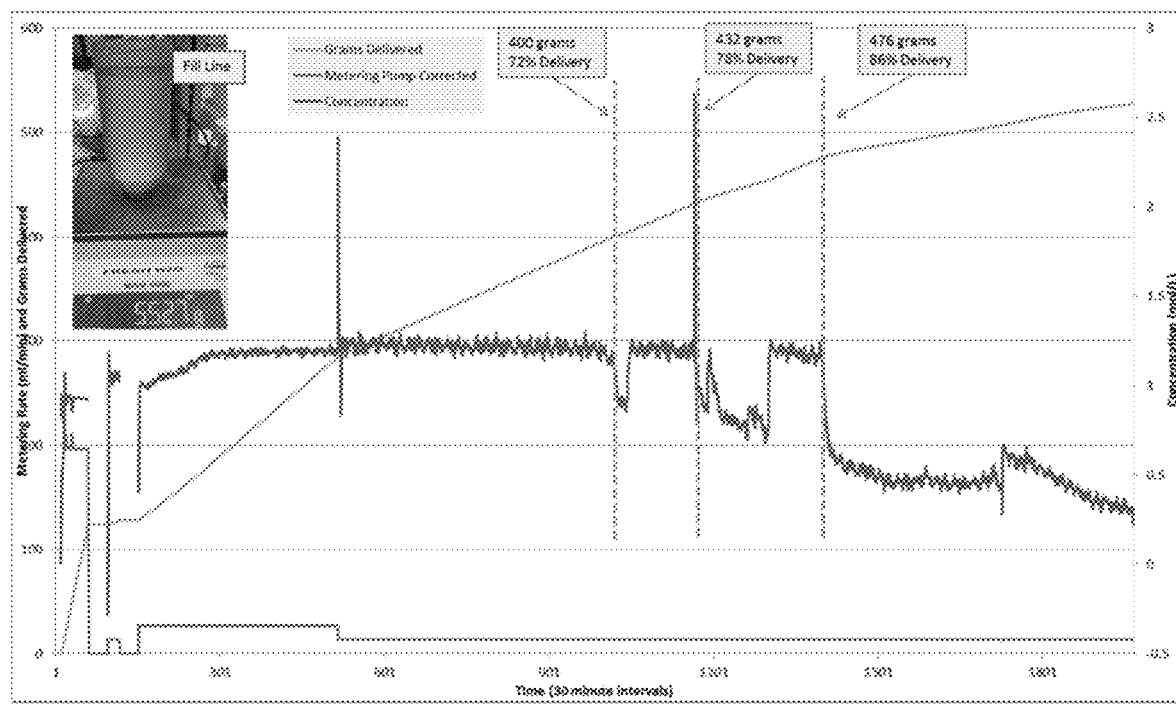
FIG. 12 is a graph showing delivery of sodium bicarbonate from Koncen using a maximum fill volume.

FIG. 12 is a graph showing the sodium bicarbonate concentrate concentration, the mass of sodium bicarbonate delivered, and the metering pump rate as tested using the Fisher Scientific sodium bicarbonate using a maximum fill volume of 553 g. The top line in FIG. 12 is the total mass of sodium bicarbonate delivered, the center line is the concentration of the sodium bicarbonate, and the bottom line is the metering pump rate. As illustrated in FIG. 12, the concentrate reached at generally steady concentration after about 45 minutes. Breakthroughs occurred during the experiment prior to depletion of the sodium bicarbonate, resulting in a lower delivery efficiency. The total mass delivered at the point at which the first breakthrough occurred was 400 g, or a 72% efficiency. The total mass delivered at the point at which the second breakthrough occurred was 432 g, or a 78% efficiency. The total mass delivered at the point at which the third breakthrough occurred was 476 g, or an 86% efficiency.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. An infusate container for use in dialysis, comprising:
a container body;
a cap removably connected to a top portion of the container body; the cap having a fluid connector for connection to a dialysis system;
a draw tube downwardly extending through the container body; the draw tube connected to the cap; the draw tube downwardly extending through a filter and into a bottom portion of the container body;
the filter connected to the draw tube; the filter separating the container body into the top portion and a bottom portion; and
further comprising at least one support member on an interior of the infusate container, wherein a first end of the at least one support member is connected to the draw tube and a second end of the at least one support member in is contact with the container body.

2. The infusate container of claim 1, further comprising an inwardly tapering portion in the bottom portion of the infusate container.

3. The infusate container of claim 1, further comprising a removable film on a top side of the cap.

4. The infusate container of claim 1, the filter connected to the container body by any of glue, heat sealing, or welding.

5. The infusate container of claim 1, wherein the filter is either a mesh or a frit filter.

6. The infusate container of claim 1, wherein the fluid connector is a bi-channel connector.

7. The infusate container of claim 6, wherein the bi-channel connector has a first channel fluidly connected to the draw tube.

8. The infusate container of claim 1, further comprising a visual indicator indicating a substance inside the container body.

9. The infusate container of claim 8, wherein the visual indicator is a colored band.

10. The infusate container of claim 1, wherein the draw tube is molded to the cap.

11. The infusate container of claim 1, the at least one support member preventing the draw tube from contacting a base of the infusate container.

12. A dialysis system, comprising:
a dialysis machine comprising:
(i) a dialysate flow path;
(ii) one or more fluid connectors fluidly connecting one or more infusate containers to the dialysate flow path wherein the infusate containers comprise: a container body; a cap removably connected to a top portion of the container body; the cap having a fluid connector for connection to the dialysis system; a draw tube downwardly extending through the container body; the draw tube connected to the cap; and a filter connected to the draw tube; the filter separating the container body into the top portion and a bottom portion; the draw tube downwardly extending through the filter and into the bottom portion; wherein the infusate containers contain a solid infusate in the top portion; the one or more infusate containers each comprising at least one support member on an interior of the infusate container, wherein a first end of the at least one support member is connected to the draw tube and a second end of the at least one support member in is contact with the container body; and
(iii) at least one pump connected to a fluid line fluidly connected to one or more fluid connectors.

13. The dialysis system of claim 12, wherein the fluid connector is a bi-channel connector.

14. The dialysis system of claim 13, wherein a first channel of the bi-channel connector fluidly connects the draw tube to a first fluid line; and wherein a second channel of the bi-channel connector fluidly connects an infusate container to a second fluid line.

15. The dialysis system of claim 12, wherein an infusate container contains sodium chloride, sodium bicarbonate, a cation infusate, or combinations thereof.

16. The dialysis system of claim 12, further comprising an infusate frame, the infusate frame housing the infusate containers.

17. The dialysis system of claim 16, the infusate frame having one or more apertures for housing the one or more infusate containers; the one or more apertures sized or shaped complementary to the one or more infusate containers.

18. The dialysis system of claim 12, the at least one support member preventing the draw tube from contacting a base of the one or more infusate containers.

19. A method, comprising the steps of:
  flowing water into an infusate container for use in dialysis, the infusate container comprising: a container body; a cap removably connected to a top portion of the container body; the cap having a fluid connector for connection to a dialysis system; a draw tube downwardly extending through the container body; the draw tube connected to the cap; a filter connected to the draw tube; the filter separating the container body into the top portion and a bottom portion of the container body; the draw tube downwardly extending through the filter; and at least one support member on an interior of the infusate container, wherein a first end of the at least one support member is connected to the draw tube and a second end of the at least one support member in is contact with the container body; wherein the infusate container contains a solid infusate in the top portion;
  dissolving at least a portion of the solid infusate to make an infusate solution;
  filtering the infusate solution and retaining the infusate solution in the bottom portion of the container body; and
  flowing the infusate solution into a dialysate flow path.

20. The method of claim 19, wherein the step of flowing water into the infusate container further comprises flowing water through a first channel of a bi-channel connector; and wherein the step of flowing the infusate solution into the dialysate flow path comprises flowing the infusate solution through a second channel of the bi-channel connector.

21. The method of claim 19, wherein the step of dissolving at least the portion of the solid infusate to make the infusate solution comprises making a saturated infusate solution.

22. The method of claim 19, wherein an infusate is sodium bicarbonate, sodium chloride, a cation infusate, or a combination thereof.

23. The method of claim 19, the at least one support member preventing the draw tube from contacting a base of the infusate container.

\* \* \* \* \*